(12) United States Patent
Parodi

(10) Patent No.: US 6,641,573 B1
(45) Date of Patent: *Nov. 4, 2003

(54) DEVICE AND METHOD OF GUIDE WIRE BALLOON INFLATION AND DEFLATION TO PREVENT CEREBRAL EMBOLIZATION DURING CAROTID STENTING

(75) Inventor: Juan Carlos Parodi, Buenos Aires (AR)

(73) Assignee: Arteria Medical Science, Inc., San Francisco, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 158 days.

(21) Appl. No.: 09/611,042

(22) Filed: Jul. 6, 2000

Related U.S. Application Data

(63) Continuation-in-part of application No. 09/533,318, filed on Mar. 22, 2000, now abandoned.
(60) Provisional application No. 60/126,556, filed on Mar. 26, 1999, and provisional application No. 60/126,208, filed on Mar. 25, 1999.

(51) Int. Cl.[7] .............................................. A61M 29/00
(52) U.S. Cl. .................... 604/510; 604/96.01; 604/264; 604/164.13; 604/192
(58) Field of Search ........................... 604/97.01, 96.01, 604/99.01, 164.01, 164.02, 164.13, 165.01, 523, 533, 264, 500, 506–510, 97.02, 97.03, 98.01, 98.02, 99.02, 103.04; 606/191, 192, 194; 623/1.11

(56) References Cited

U.S. PATENT DOCUMENTS

| | | | | |
|---|---|---|---|---|
| 4,964,409 A | * | 10/1990 | Tremulis | 128/657 |
| 5,342,303 A | * | 8/1994 | Ghaerzadeh | 604/96 |
| 5,344,414 A | * | 9/1994 | Lopez et al. | 604/283 |
| 5,348,537 A | | 9/1994 | Wiesner et al. | |
| 5,359,995 A | * | 11/1994 | Sewell, Jr. | 128/20 |
| 5,378,236 A | | 1/1995 | Seifert | 604/96 |
| 5,545,133 A | * | 8/1996 | Burns et al. | 604/96 |
| 5,557,905 A | | 9/1996 | Harding | |
| 5,779,688 A | | 7/1998 | Imran et al. | 604/283 |
| 5,833,650 A | | 11/1998 | Imran | 604/53 |
| 6,517,514 B1 | * | 2/2003 | Campbell | 604/96 |

FOREIGN PATENT DOCUMENTS

| WO | WO 97/04829 | 2/1997 | ........ A61M/29/00 |
|---|---|---|---|

\* cited by examiner

*Primary Examiner*—Long V. Le
*Assistant Examiner*—Ann Y Lam
(74) *Attorney, Agent, or Firm*—Luce, Forward, Hamilton & Scripps; Nicola A. Pisano

(57) ABSTRACT

A device and method for inflating and deflating a balloon, used to protect the cerebrum against emboli, during carotid stenting, is provided wherein the device comprises a balloon carried on a guide wire and wherein inflation can be accomplished without the need of a port on the guide wire, so that coaxial systems may be applied over the guide wire. The device comprises a guide wire having an interior lumen and a balloon that communicates with the lumen. A core segment is inserted into the open end of the guide wire, and serves as a piston to inflate the balloon after saline is introduced into the lumen. A locking mechanism is provided to retain the core segment in position during the procedure. Coaxial systems, such as balloon catheters and stent delivery systems, can be applied over the guide wire without deflating the guide wire balloon.

27 Claims, 5 Drawing Sheets

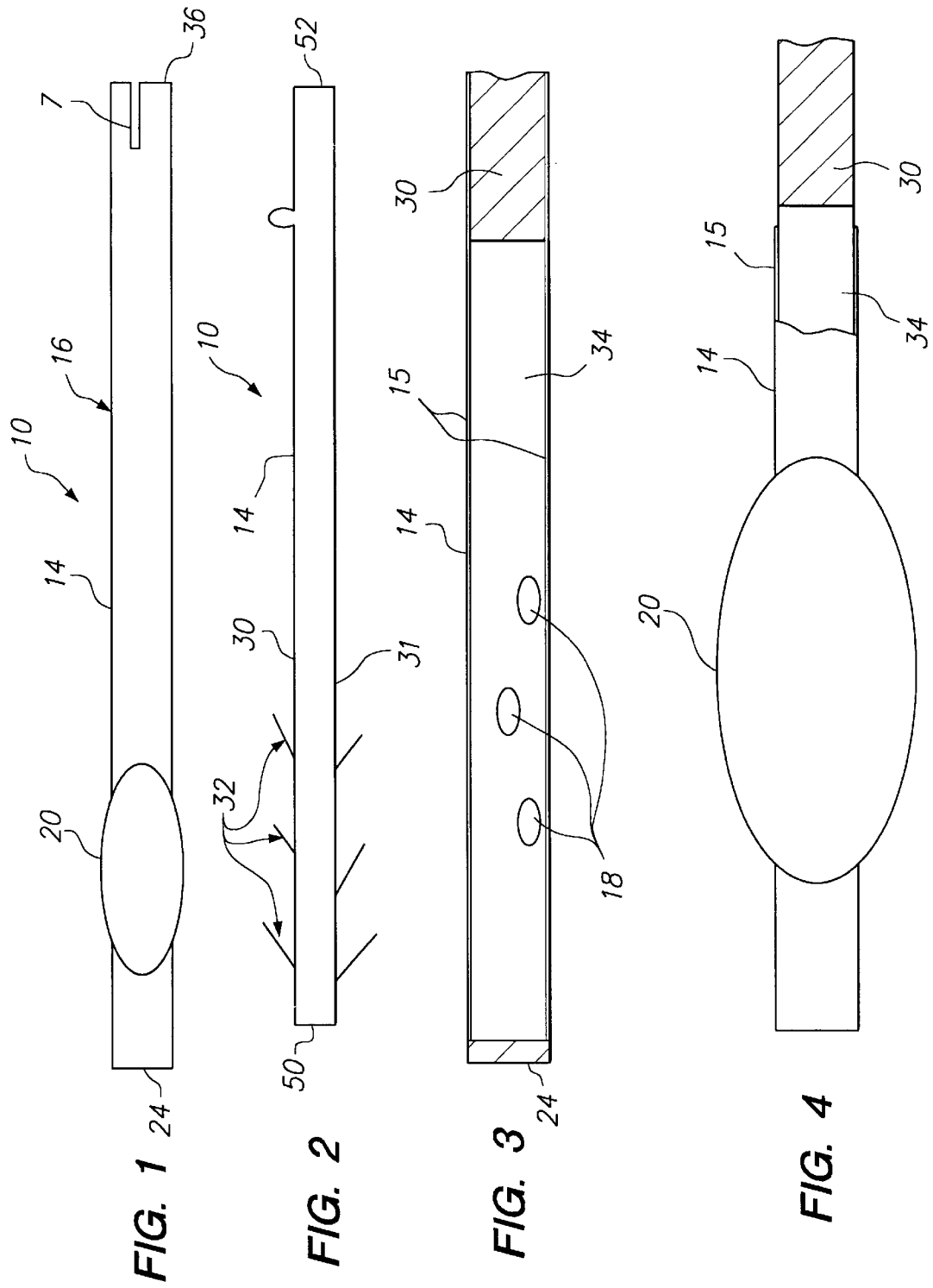

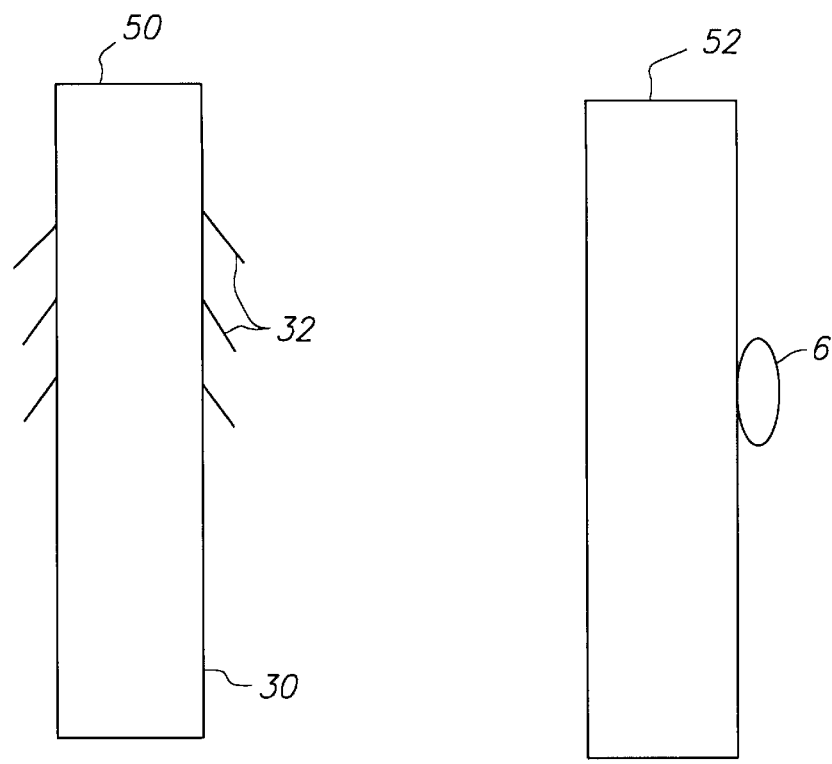
FIG. 7  FIG. 8
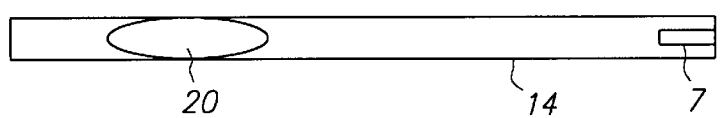
FIG. 9
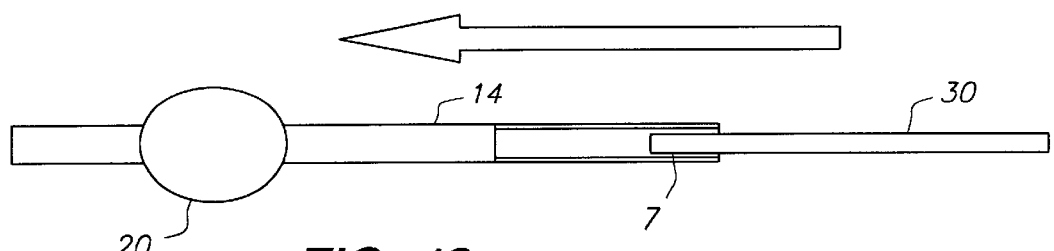
FIG. 10

DEVICE AND METHOD OF GUIDE WIRE BALLOON INFLATION AND DEFLATION TO PREVENT CEREBRAL EMBOLIZATION DURING CAROTID STENTING

REFERENCE TO RELATED APPLICATIONS

The present application is a continuation-in-part of U.S. patent application Ser. No. 09/533,318 filed Mar. 22, 2000, now abandoned which claims benefit from the filing date of provisional U.S. patent application Ser. No. 60/126,556 filed Mar. 26, 1999, and further claims benefit from the filing date of provisional U.S. patent application Ser. No. 60/126,208 filed Mar. 25, 1999.

FIELD OF THE INVENTION

This invention relates to a device and method for inflating and deflating a balloon used to protect the cerebrum against emboli during carotid stenting, where the balloon is carried on a guide wire and where the inflation can be accomplished without the need of a port on the guide wire. Coaxial systems may be applied over the guide wire, because the outside of the guide wire is of a smooth surface with no ports.

The device comprises a guide wire, having a lumen inside the guide wire. The guide wire has one end occluded and the other end open, and has a balloon at the occluded end. The guide wire has two or three orifices, each extending from the exterior of the guide wire to reach the lumen of the guide wire. Thus, the lumen of the guide wire is connected to the inside of the balloon through these orifices. The area of the guide wire with the orifices is covered by a silicon or polyurethane balloon. A core segment is inserted into the open end of the guide wire to the closed end of the guide wire before the orifices on the guide wire are covered by a balloon. The core segment may be removed from the guide wire when the open end of the guide wire is inside a basin full of normal saline mixed with non-ionic contrast media solution. When the core segment is removed, it creates a vacuum inside the lumen of the guide wire which is filled immediately with the solution. Then, the core segment is gently advanced until the balloon is fully distended. Through a locking mechanism, the core segment is kept in position during the time needed for the procedure. Coaxial systems, such as balloon catheter and stent delivery systems, may be applied over the guide wire. After the procedure which may generate emboli is completed, the core segment is unlocked and retrieved and the balloon is thereby deflated.

BACKGROUND OF THE INVENTION

Although traditionally conventional open surgery has been used in treatments of vascular diseases, such as stenosis of the carotid artery, nowadays endovascular treatments are gaining acceptance. Endovascular treatments are carried out in the lumen of the vascular duct and have the advantage of being less aggressive than the conventional open surgery posing less risk to the patient because it can be performed under limited local anesthesia and without surgery.

Where there is stenosis of an artery, such as the common carotid artery, the internal carotid artery or the external carotid artery, the vascular wall of the artery is affected by a pathologic narrowing that prevents the blood stream from flowing normally. A common treatment consists of endovascular angioplasty, where an angioplasty balloon is inserted into the lumen of the blood vessel and the angioplasty balloon is expanded in order to expand the area having the stenosis. If necessary, a stent is placed to cover the afflicted area.

Balloon angioplasty and stenting are a rapidly growing field in vascular intervention. The main and dreadful complication of carotid balloon angioplasty and stenting is cerebral embolization. Several studies have shown that the incidence of embolization is high during these procedures.

The problem in this treatment is that emboli can be formed during the course of the procedure which can rapidly reach the brain and cause injury and death. Emboli are especially prone to be formed when the angioplasty balloon is expanded or while the stent is placed and expanded.

Investigators, such as Jack Theron, used a balloon to prevent particles generated in the affected area from reaching the brain. U.S. Pat. No. 5,833,650 of inventor Imran, entitled Catheter Apparatus and Method for Treating Occluding Vessels, issued Nov. 10, 1998. The Imran patent described a system to achieve cerebral protection using a guide wire and inflated balloons, which allowed the advancement over the guide wire of a coaxial system of balloon angioplasty catheters and stent delivery systems. The use of occlusion balloons to protect the brain during carotid balloon angioplasty and stenting (CBAS) was presented publicly by Theron in Milwaukee in 1994.

Difficulty exists in keeping the occlusion balloon inflated and undisturbed when changing the coaxial systems. The ports with valves on a guide wire prevent advancement of coaxial systems, that very often need to be changed. For instance, different balloon diameters may be needed in the procedure. Sometimes, one balloon may need to be replaced with a balloon of a different diameter. Systems to deploy a stent and systems to expand a stent with a balloon also may require coaxial systems. The presence of a port on the guide wire would obligate the operator to deflate and remove the guide wire every time he needed to exchange the coaxial system, such as, for example, either to use a different balloon diameter catheter or to advance a delivery system for stent deployment.

Therefore, there is needed in the art a device and method that allows for the inflation and deflation, without the need of a port on the guide wire, of a balloon carried on a guide wire. There is needed a device and method which allow for the use of coaxial systems to be placed over the guide wire to allow for the use and placement of instrumentation needed during the medical procedure without the necessity of deflating the balloon and removing the guide wire.

The present invention recognizes that a balloon situated on a hollow guide wire, where the hollow guide wire permits insertion of a core segment into the lumen of the guide wire, will allow for easy and convenient inflation and deflation of the balloon while permitting coaxial systems to be introduced over the guide wire. Thus, the present invention allows for the rapid exchange of coaxial systems without the need to disconnect or connect ports which in prior art have been attached to the guide wire.

SUMMARY OF THE INVENTION

The invention comprises a hollow guide wire with a plurality of orifices extending from the exterior of the guide wire to its lumen, an attached balloon which covers the orifices and a core segment. The core segment may be inserted into the lumen of the guide wire and then removed from the lumen of the guide wire when the open end of the guide wire is inserted in a solution. The core segment is sized to fit snugly within the lumen of the guide wire and serves as a piston to inflate the guide wire balloon.

The guide wire is provided with a closed end and an open end which form a tubular body having an internal lumen.

Near the closed end of the guide wire there is a guide wire balloon, which may be expandable against the vascular duct to occlude the blood flow.

The guide wire with attached guide wire balloon have a low profile allowing the insertion and advancement of coaxial balloon catheters and stent delivery systems over the guide wire without disturbing the inflated guide wire balloon.

In use, the operator takes the guide wire with the core segment positioned inside the lumen of the guide wire and with the guide wire balloon in its uninflated position on the guide wire, and inserts the closed end of the guide wire with the attached guide wire balloon into the patient through methods known in the art, such as percutaneously into the femoral artery. Then, the guide wire balloon is advanced through the vessel and positioned at the appropriate location in the patient. The open end of the guide wire is inserted inside a solution. A solution of normal saline mixed with non-ionic contrast media may be used. In particular, a solution consisting of 50% normal saline and 50% non-ionic contrast media may be used. The core segment is removed from the lumen of the guide wire with the open end of the guide wire inserted within the solution. The solution fills the lumen of the guide wire. Then, the core segment is gently advanced toward the guide wire balloon until the guide wire balloon is fully dilated. The guide wire balloon is thus expanded against the vascular walls. Once the guide wire balloon is inflated, the core segment is fixed in position within the guide wire by a locking mechanism which does not increase the profile of the guide wire. Therefore, the advancement of coaxial systems over the guide wire is allowed. Coaxial systems may be exchanged without the need to deflate the guide wire balloon.

BRIEF DESCRIPTION OF THE DRAWINGS

FIG. 1 is a view of the guide wire with the guide wire balloon in its deflated position.

FIG. 2 is a view of the core segment which has not been inserted into the lumen of the guide wire.

FIG. 3 is a longitudinal cross-section of the hollow guide wire showing the orifices of the guide wire.

FIG. 4 is a view, partly in section, of the guide wire showing an inflated guide wire balloon attached thereto.

FIG. 7 is a view of the distal end of one embodiment of the core segment, showing three rings, which are a sealing mechanism.

FIG. 8 is a view of the operator end of one embodiment of the core segment, showing the knob, which is a part of the locking mechanism.

FIGS. 9 and 10 are views showing the apparatus of the present invention with the balloon in the uninflated and inflated configurations, respectively.

DESCRIPTION OF THE PREFERRED EMBODIMENTS

Figure 5:
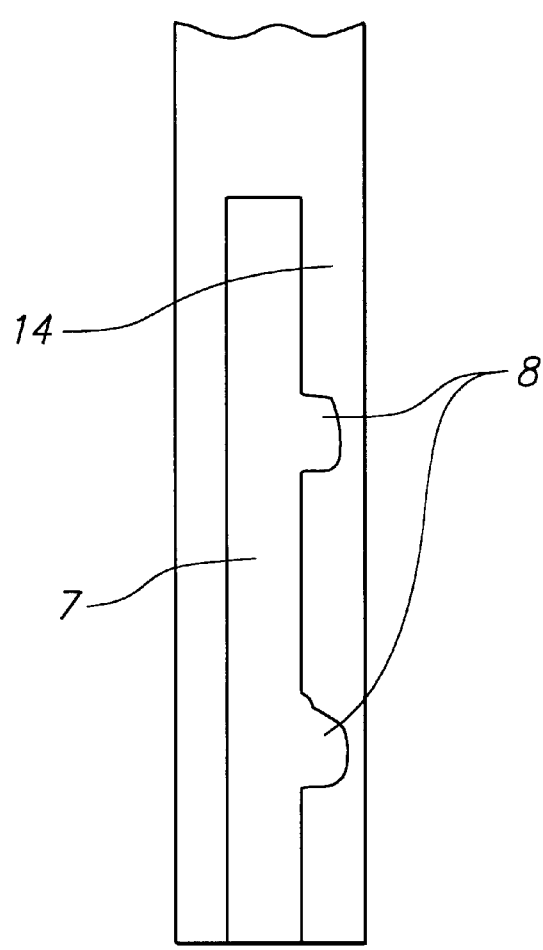
FIG. 5 is a view of the open end of the guide wire showing an embodiment of the guide wire with a groove and two spaces, which are part of a locking mechanism.

Referring to FIGS. 1 to 4, the balloon inflation device (10) of the present invention, for use in carotid angioplasty, comprises a guide wire (14) having a guide wire balloon (20) near the closed end (24) of the guide wire and a core segment (30) which may be inserted into the lumen (34) of the guide wire. The guide wire balloon (20) may be integral with the guide wire (14) and may be formed on the guide wire by means known in the art. The core segment (30) may be moved in an axial direction in the lumen of the guide wire. In a preferred embodiment for use with carotid stenting, the length of the guide wire is 2.3 meters and the length of the core is 2.4 meters. However, other lengths of the guide wire and core may be used.

The guide wire (14) comprises a cylinder body (16) having a closed end (24) and an open end (36). The cylinder body (16) of the guide wire (14) forms by its inner wall (15) in its interior a lumen (34) of the guide wire. Preferably, the guide wire is made of metal. As shown in FIG. 3, the guide wire (14) has a plurality of orifices (18) near its closed end. In a preferred embodiment the guide wire (14) has two or three such orifices (18). The orifices (18) are openings which extend from the outside of the guide ire (14) into the lumen (34) of the guide wire. Preferably, these orifices (18) are made in different segments of different circumferences of the guide wire. Preferably, these orifices are 1 or 2 mm apart, one from each other. The area of the guide wire with the orifices (18) is covered by the guide wire balloon (20), preferably made of silicon or polyurethane.

Preferably, the core segment (30) is inserted into the guide wire (14) before the guide wire balloon (20) is placed to cover the orifices (18) of the guide wire (14). As shown in FIG. 2, a core segment (30) comprises a solid body (31) and has an operator end (52) and a distal end (50). The core segment (30) corresponds to the lumen of the guide wire. The core segment (30) is inserted into the lumen (34) of the guide wire, so that the distal end (50) of the core segment (30) first enters the lumen (34) of the guide wire. The core segment (30) provides rigidity to the guide wire (14). The core segment (30) is slightly smaller in width than the lumen (34) of the guide (14) so as to allow the advancement of the core segment (30) within the lumen (34) of the guide wire (14), but must be of sufficient width so as to not allow seepage of fluid around the core segment (34), when the core segment (34) is properly sealed within the lumen (34) of the guide wire 914) by a sealing mechanism. Such sealing may be accomplished by a variety of means.

The core segment (34) may be fitted with a plurality of rings (32), which attach around the core segment, or the core segment may be covered at its distal end portion with a layer of sealing material, the rings (32) or the sealing material, being made of silicone or other appropriate material, such as TEFLON™, to provide a watertight seal of the core segment (34) with the inner wall (15) of the guide wire to prevent leakage of fluid around the core segment (30).

The core segment (30) is inserted within the guide wire (14) so as to seal the guide wire (14) in the same way a piston adapts to a cylinder. The core segment (30) is sized in dimension such that there is no noticeable gap between the core segment (30) and the guide wire (14). If the fitting of the core segment (30) within the lumen (34) of the guide wire (14) is not watertight, solution would leak, allowing the guide wire balloon (20) to deflate. Therefore, the core segment (30) must be fitted within the lumen (34) of the guide wire (14), and such fitting may employ the use of seals, rings or the like, so as to be watertight to prevent leakage of fluid around the core segment when the core segment (30) is within the guide wire (14).

Rings, such as those made of TEFLON™, silicone or the like, may be inserted into the lumen (34) of the guide wire (14) and placed so as to seal the lumen (34) of the guide wire 914) against the core segment (30), when the core segment (30) is within the guide wire (14). Alternatively, as shown in FIG. 2, rings (32), such as those made of TEFLON™, silicone or the like, may be placed at the distal end (50) of the core segment (30), so that when the core segment (30) is within the guide wire (14) there is a watertight seal between the sides of the core segment and the inner wall (15) of the guide wire (14).

Preferably, two or three rings either within the end of the guide wire (14) or attached to the outside distal end (50) of the core segment (30) may be used to accomplish this watertight seal. Alternatively, the distal end (50) of the core segment (30) may be covered with silicone or TEFLON™ to seal the core segment so that no fluid may leak around the core segment (30) when the core segment (30) is positioned within the lumen (34) of the guide wire (14).

Thus, the guide wire (14) has a low profile, because the core segment (30) used to inflate and deflate the guide wire balloon (20) is inserted into the lumen (34) of the guide wire (14) and therefore does not increase the profile of the guide wire. The guide wire (14) avoids the use of a portion for inflation of the guide wire balloon (20), as such port is described in the prior art, which port would increase the profile of the guide wire. Therefore, coaxial systems can be applied over the guide wire (14) of this invention. Typically, balloon catheters and stent delivery systems may be applied over the guide wire (14) without having to deflate the guide wire balloon.

As shown in FIG. 8, the guide wire (14) and core segment (30) may be fitted with a locking mechanism to achieve, when needed, an immobilization of the core segment (30) in relation to the guide wire (14). Such locking mechanism may be achieved without significantly increasing the profile of the guide wire (14). In a preferred embodiment of a locking mechanism, the core segment (30) has a very small prominent knob (6), preferably made of metal or other biocompatible material, which does not extend beyond the outer diameter of the guide wire (14) and which is located near the operator end (52) of the core segment (30). In this embodiment of the locking mechanism, the guide wire (14) has a narrow groove (7), preferably of 3 cm length, which extends longitudinally from the open end (36) of the guide wire (14) toward the closed end (24) of the guide wire (14).

Referring to FIG. 7, the groove (7) has a plurality of side housing spaces (8), preferably 3 cm apart, one to each other. Preferably, there are two or three side housing spaces (8). Preferably, each side housing space (8) is perpendicular to the groove (7) in the guide wire (14). The knob (6) fits within a selected side housing space (8). The core segment (30) is immobilized at the chosen level by rotating the core segment (30) until the knob (6) of the core segment enters the side housing space (8) of the guide wire (14), which thereby locks the core segment in its position within the lumen (34) of the guide wire (14).

Figure 6:
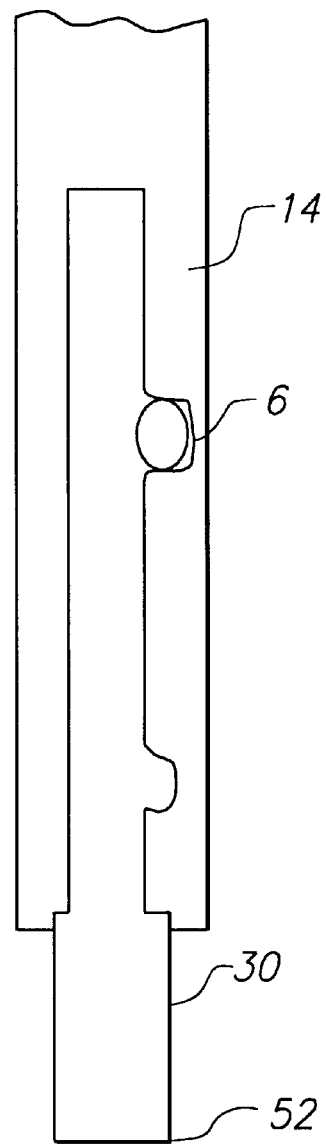
FIG. 6 is a view of a portion of one embodiment of the invention, showing the open end of the guide wire with the core segment inserted into the lumen of the guide wire, with the knob of the core segment engaging one of the housing spaces of the guide wire to immobilize the core segment in its locked position.

In use, after the core segment (30) has been inserted into the open end of the guide wire and positioned, it may be locked and kept immobilized to keep the balloon inflated, as illustrated in FIG. 6. In particular, the knob (6) of the core segment (30) engages one of the housing spaces (8) of the guide wire (14) when the core segment (30) is in its locked position within the guide wire (14). The mechanism of locking consists of moving the core segment inside the guide wire (14) so as to position the knob (6) at the same point in the circumferences as the groove (7) of the guide wire.

Once the knob (6) enters the groove (7), attention is paid to the guide wire balloon (20) to determine that it is fully inflated. If the balloon is fully inflated the core segment (30) should be locked in position up to the end of the procedure to keep the balloon fully inflated. The core is locked within the guide wire by a gentle rotation of the core segment (30) to install the knob (6) inside the side housing space (8).

After the medical procedure is carried out, the core segment (30) is unlocked and the guide wire balloon (20) is deflated by reversing the rotation of the core segment (30) to release the knob (6) of the core segment from the housing space (8) of the guide wire (14). Thus, the guide wire balloon (20) has a first configuration of reduced size in its uninflated state (FIG. 9) and a second configuration of expanded size in its inflated state (FIG. 10), the guide wire balloon (20) being expandable from its first configuration to its second configuration.

In use the guide wire balloon (20) is in its uninflated configuration when the guide wire (14) with guide wire balloon (20) is introduced into the patient. At the appropriate time when the operator chooses to expand the guide wire balloon (20) against the vascular duct to occlude the blood flow the guide wire balloon may b expanded according to the following actions. In carotid stenting, the guide wire may be positioned at the desired location of occlusion, such as in the internal carotid artery beyond the stenosis, before the guide wire balloon (20) is inflated.

The open end (36) of the guide wire (14) is inserted inside the desired solution, used to inflate the guide wire balloon, such as a normal saline mixed with non-ionic contrast media. Preferably, a solution consisting of 50% normal saline and 50% non-ionic contrast media is used. The solution may be kept available inside a basin. The core segment (30) is removed from the lumen (34) of the guide wire (14) with the open end of the guide wire (14) inserted within the saline/contrast media solution. When the core segment (30) is removed it creates a vacuum inside the lumen (34) of the guide wire (14) which is then immediately filled by the solution. The saline/contrast media solution fills the lumen (34) of the guide wire (14).

Figure 11:
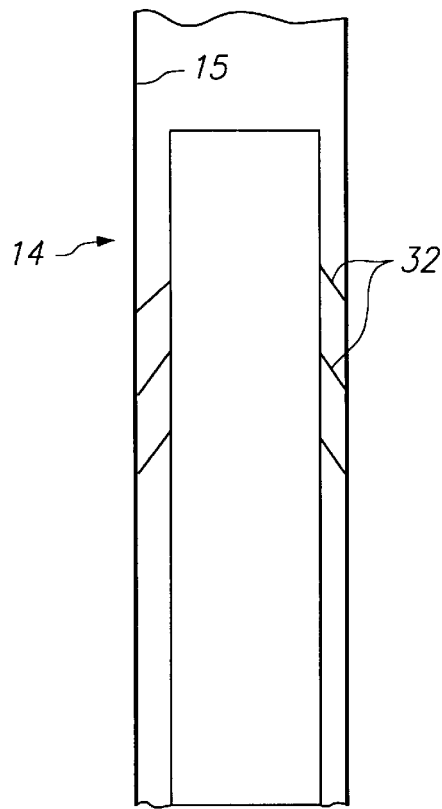
FIGS. 11 and 12 are longitudinal cross-sections of the portion of guide wire containing the distal end of the core segment.
Figure 12:
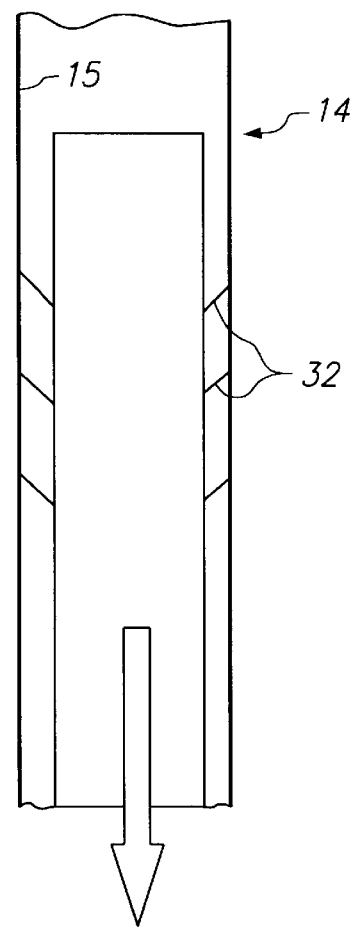

As illustrated in FIG. 10, the core segment (30 then is gently advanced toward the guide wire balloon (20) until the guide wire balloon (20) is fully dilated. The solution flows through the orifices (18) of the guide wire (14) into the guide wire balloon (20) to inflate the guide wire balloon (20). As further depicted in FIG. 11, the distal end of the core first is advanced inside the hollow guidewire (14) so that the rings (32) follow the direction of the core. Once the final position has been reached, the rings are reversed by gently pulling the core out, thereby sealing the guidewire cavity. The guide wire balloon (20) is thus expanded against the vascular walls. The core segment (30) may be locked in the guide wire (14) and kept in position to maintain the inflation of the guide wire balloon (20) during the time needed for the procedure.

After expansion of the guide wire balloon (20), endovascular procedures, such as carotid stenting, may be performed. For example, a catheter, balloon of angioplasty, a stent or any other suitable apparatus or instrument may be passed by way of a coaxial system over the guide wire (14) to reach the appropriate area of the vascular walls for appropriate treatment.

Once the procedure is finished and when the expanded guide wire balloon (20) is no longer needed in its expanded position, the core segment (30) is unlocked and withdrawn from the lumen (34) of the guide wire (14) until the guide wire balloon (20) is completely deflated. Thus, the guide wire balloon may be returned to its uninflated position by removing the core segment (30) from the open end (36) of the guide wire (14).

In particular, a new method for inflating and deflating a guide wire balloon (20) is described below, wherein the operator uses a balloon inflation device (10) in which a core segment (30) has been inserted into the open end (36) of the guide wire (14) and positioned at the closed end (24) of the guide wire (14), and the orifices (18) on the guide wire (14) are covered by a guide wire balloon (20).

The operator inserts the closed end (24) of the guide wire (14) into the patient, by means known in the art, such as percutaneously into the femoral artery and then positions the guide wire balloon at the appropriate location of intended use in the body. The core segment (30) may be removed from the guide wire (14) when the open end (36) of the guide wire (14) is inside a basin full of solution, such as normal saline mixed with non-ionic contrast media. When the core segment (30) is removed from the lumen (34) of the guide wire (14), it creates a vacuum inside the lumen (34) of the guide wire which is filled immediately with the solution. Then, the core segment (30) is gently advanced toward the guide wire balloon (20) until the guide wire balloon (20) is fully distended. Through a locking mechanism the core segment (30) is kept in position during the time needed for the procedure. Coaxial systems, such as balloon catheter and stent delivery systems, may be applied over the guide wire (14) without deflating the guide wire balloon (20). After the procedure, which may generate emboli, is completed, the core segment (30) is unlocked and retrieved and the guide wire balloon (20) is thereby deflated.

In alternative embodiments of the invention, the methods and apparatus can be used in other procedures and repairs of the anatomy, where there is a need to inflate an occlusion balloon to protect against dangerous emboli. In such procedures, the convenient method and apparatus for the inflation and deflation of a balloon may be likewise useful.

Figure 13:
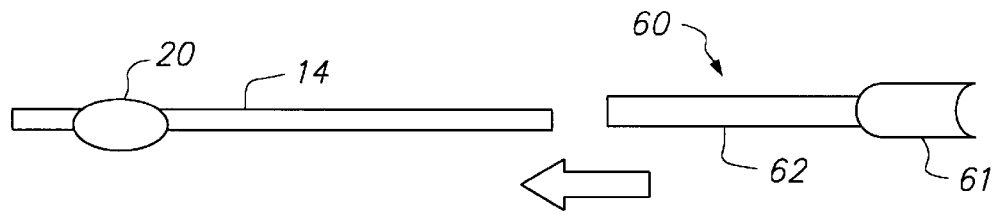
FIGS. 13 through 17 are views depicting an alternative method of inflating the apparatus of the present invention.
Figure 14:
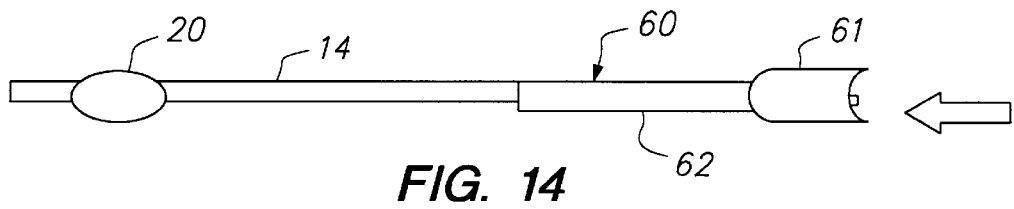
Figure 15:
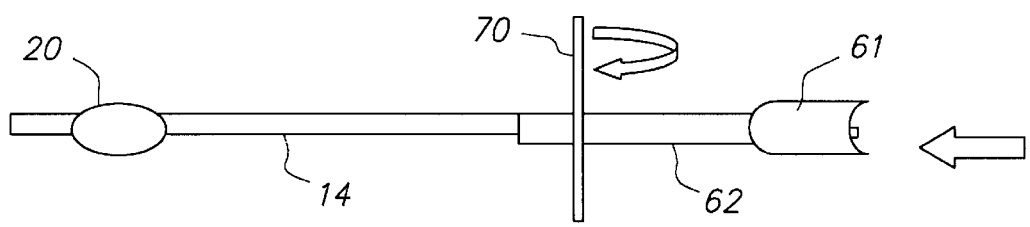

Referring to FIGS. 13 to 17, one such alternative embodiment is described. As shown in FIGS. 13 and 14, inflation device (60) comprising syringe (61) coupled to flexible and collapsible shaft (62) is advanced over guidewire (14). Syringe (61) serves for air removal and balloon inflation with a diluted contrast solution. Once the balloon (20) is inflated by operating syringe (61), a clamp (70) is applied to the soft segment of the shaft (62), thereby keeping the fluid inside of guidewire (14) and balloon (20).

Figure 16:
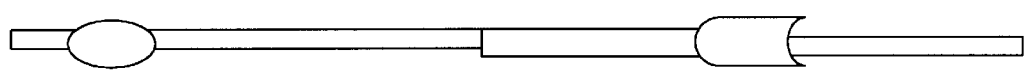
Figure 17:

As shown in FIG. 16, core segment (30) is advanced through an opening in the back of syringe (61) and inside the lumen of the shaft (62). Core segment (30) is sized to tightly seal the lumen of shaft (62) to prevent leaking of the contrast solution. Once the core segment (30) reaches the clamp (70), the clamp (70) is removed, and the core segment is advanced inside the lumen of guidewire (14), as described hereinabove. Core segment (30) is then locked in place in slot (7) of the guide wire (14). As depicted in FIG. 17, shaft (62) and syringe (61) then are removed, thereby providing a small profile over which interventional instruments may be coaxially advanced.

Having described this invention with respect to its preferred embodiments, it is to be understood that the description is not meant as a limitation since further variations or modifications may be apparent or may suggest themselves to those skilled in the art. It is intended that the present application cover such variations and modifications as fall within the scope of the appended claims.

What is claimed is:

1. A device for inflating and deflating a guide wire balloon, the device comprising:
    a guide wire having a lumen, an orifice extending from the exterior of the guide wire to the lumen, and two ends, the two ends comprising a closed end and an open end, wherein the lumen provides fluid communication between the orifice and the open end;
    an inflatable guide wire balloon coupled to the guide wire in communication with the orifice;
    a core segment disposed within the lumen of the guide wire, the core segment configured for removal from the lumen of the guide wire, thereby establishing a vacuum in the lumen that facilitates inflation of the guide wire balloon;
    a plurality of orifices extending from the exterior of the guide wire to the lumen,
    wherein the open end of the guide wire is dimensioned to permit a coaxial angioplasty balloon catheter or stent delivery catheter to be exchanged over the guide wire and at least partially over said core segment from the open end to a position just proximal of the balloon without deflating the balloon.

2. The device of claim 1, further comprising a solution in communication with the open end of the guide wire, the core segment removed from and then advanced into the lumen of the guide wire to inflate the guide wire balloon with the solution.

3. The device of claim 2, further comprising a plurality of orifices extending from the exterior of the guide wire to the lumen.

4. The device of claim 1, further comprising a locking mechanism configured to lock the core segment in a fixed position within the lumen of the guide wire to maintain the guide wire balloon in an inflated configuration.

5. The device of claim 2, further comprising a locking mechanism configured to lock the core segment in a fixed position within the lumen of the guide wire to maintain the guide wire balloon in an inflated configuration.

6. The device of claim 1, further comprising a locking mechanism configured to lock the core segment in a fixed position within the lumen of the guide wire to maintain the guide wire balloon in an inflated configuration.

7. The device of claim 4, wherein the locking mechanism is disposed within the lumen of the guide wire.

8. The device of claim 5, wherein the locking mechanism is disposed within the lumen of the guide wire.

9. The device of claim 1, further comprising a coaxial angioplasty balloon catheter or stent delivery catheter configured for exchange over the guide wire while the guide wire balloon is in an inflated configuration.

10. The device of claim 2, further comprising a coaxial angioplasty balloon catheter or stent delivery catheter configured for exchange over the guide wire while the guide wire balloon is in an inflated configuration.

11. The device of claim 1, further comprising a coaxial angioplasty balloon catheter or stent delivery catheter configured for exchange over the guide wire while the guide wire balloon is in an inflated configuration.

12. The device of claim 3, further comprising a coaxial angioplasty balloon catheter or stent delivery catheter configured for exchange over the guide wire while the guide wire balloon is in an inflated configuration.

13. The device of claim 4, further comprising a coaxial angioplasty balloon catheters or stent delivery catheter configured for exchange over the guide wire while the guide wire balloon is in an inflated configuration.

14. The device of claim 4, wherein the locking mechanism further comprises:
   a groove disposed on the guide wire, the groove extending longitudinally along the guide wire from the open end;
   a side housing space disposed on the guide wire perpendicular to the groove; and
   a knob disposed on the core segment, the knob configured to engage the housing space and lock the core segment to the guide wire.

15. The device of claim 5, wherein the locking mechanism further comprises:
   a groove disposed on the guide wire, the groove extending longitudinally along the guide wire from the open end;
   a side housing space disposed on the guide wire perpendicular to the groove; and
   a knob disposed on the core segment, the knob configured to engage the housing space and lock the core segment to the guide wire.

16. The device of claim 6, wherein the locking mechanism further comprises:
   a groove disposed on the guide wire, the groove extending longitudinally along the guide wire from the open end;
   a side housing space disposed on the guide wire perpendicular to the groove; and
   a knob disposed on the core segment, the knob configured to engage the housing space and lock the core segment to the guide wire.

17. The device of claim 4, further comprising a plurality of side housing spaces disposed on the guide wire perpendicular to the groove.

18. The device of claim 4, further comprising a further comprising a sealing mechanism configured to prevent fluid leakage around the core segment when the core segment is disposed within the guide wire.

19. The device of claim 5, further comprising a sealing mechanism configured to prevent fluid leakage around the core segment when the core segment is disposed within the guide wire.

20. The device of claim 6, further comprising a sealing mechanism to prevent fluid leakage around the core segment when the core segment is disposed within the guide wire.

21. The device of claim 3, further comprising a sealing mechanism configured to prevent fluid leakage around the core segment when the core segment is disposed within the guide wire.

22. The device of claim 21, wherein the sealing mechanism comprises a plurality of rings coupled to the core segment.

23. The device of claim 22, wherein the sealing mechanism further comprises a layer of silicone coupled to a distal end portion of the core segment to prevent leakage of fluid around the core segment.

24. A method for inflating and deflating a guide wire balloon, comprising the steps of:
   providing apparatus comprising a guide wire having a lumen, an open end, and a closed end, an inflatable guide wire balloon coupled to the guide wire, and a core segment disposed within the lumen;
   inserting the closed end of the guide wire into a patient's vessel;
   situating the guide wire balloon at a position of intended use;
   inserting the open end of the guide wire into a solution;
   removing, at least partially, the core segment from the lumen of the guide wire to cause the solution to move into the lumen of the guide wire to facilitate inflation of the guide wire balloon;
   advancing the core segment toward the guide wire balloon until the guide wire balloon is inflated; and
   exchanging a coaxial angioplasty balloon catheter or stent delivery catheter over the guide wire from the open end to a position just proximal of the balloon without deflating the balloon.

25. The method of claim 24, further comprising the step of:
   locking the core segment within the guide wire to maintain inflation of the guide wire balloon.

26. The method of claim 25, further comprising the step of:
   unlocking the core segment within the guide wire; and
   withdrawing the core segment from the lumen of the guide wire to allow deflation of the guide wire balloon.

27. The method of claim 24, further comprising the step of:
   advancing a coaxial angioplasty balloon catheter or stent delivery catheter over the guide wire without deflating the guide wire balloon.

* * * * *